(12) United States Patent
Irie et al.

(10) Patent No.: US 12,247,951 B2
(45) Date of Patent: Mar. 11, 2025

(54) DETECTION SYSTEM AND DETECTION METHOD

(71) Applicant: MITSUMI ELECTRIC CO., LTD., Tokyo (JP)

(72) Inventors: Takahiko Irie, Tokyo (JP); Shigenori Inamoto, Tokyo (JP); Kenta Ueda, Tokyo (JP)

(73) Assignee: MITSUMI ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 17/646,643

(22) Filed: Dec. 30, 2021

(65) Prior Publication Data
US 2022/0120716 A1 Apr. 21, 2022

Related U.S. Application Data

(63) Continuation of application No. 16/609,195, filed as application No. PCT/JP2018/013498 on Mar. 29, 2018, now Pat. No. 11,249,052.

(30) Foreign Application Priority Data

Apr. 28, 2017 (JP) ................. 2017-090620

(51) Int. Cl.
*G01N 29/12* (2006.01)
(52) U.S. Cl.
CPC .................. *G01N 29/12* (2013.01)
(58) Field of Classification Search
CPC .................................................... G01N 29/12
See application file for complete search history.

(56) References Cited

U.S. PATENT DOCUMENTS

| 4,542,639 | A | 9/1985 | Cawley et al. |
| 5,003,824 | A | 4/1991 | Fukada et al. |
| 5,048,320 | A | 9/1991 | Mitsuhashi et al. |
| 5,533,381 | A | 7/1996 | Seale |

(Continued)

FOREIGN PATENT DOCUMENTS

| EP | 2728321 A1 * | 5/2014 | ............. G01H 3/005 |
| GB | 946589 A | 1/1964 | |

(Continued)

OTHER PUBLICATIONS

Chain link of fence, 2012, Chris (Year: 2012).*
(Continued)

*Primary Examiner* — Lina Cordero
*Assistant Examiner* — Lyudmila Zaykova-Feldman
(74) *Attorney, Agent, or Firm* — McCoy Russell LLP

(57) ABSTRACT

A detection system contains a sensing device including a vibration unit for applying vibration to the inspection target, the vibration unit attached to the inspection target, a driving circuit for supplying an electric signal to the vibration unit for driving the vibration unit and a sensor for detecting vibration of the inspection target caused by the vibration applied from the vibration unit; and a detection processing device for receiving vibration information related to the vibration of the inspection target detected by the sensor from the sensing device and detecting the state change of the inspection target based on the vibration information. The vibration unit includes a coil, a spring, and a magnet.

13 Claims, 10 Drawing Sheets

(56) References Cited

U.S. PATENT DOCUMENTS

| | | | |
|---|---|---|---|
| 5,847,817 A * | 12/1998 | Zediker | G01S 7/4911 |
| | | | 356/28.5 |
| 6,488,117 B1 | 12/2002 | Owen | |
| 2005/0078316 A1 * | 4/2005 | Ronnekleiv | G01D 5/35312 |
| | | | 356/478 |
| 2008/0148858 A1 | 6/2008 | Kasik et al. | |
| 2009/0306802 A1 * | 12/2009 | Cone | G06F 30/13 |
| | | | 700/98 |
| 2010/0102646 A1 * | 4/2010 | Masami | H02K 33/16 |
| | | | 310/29 |
| 2010/0226543 A1 * | 9/2010 | Zalevsky | G01B 9/02083 |
| | | | 382/107 |
| 2010/0315185 A1 * | 12/2010 | Kagami | H02K 33/16 |
| | | | 335/229 |
| 2011/0205647 A1 * | 8/2011 | Osaka | F16F 1/021 |
| | | | 267/161 |
| 2012/0209545 A1 * | 8/2012 | Humphries | G01H 13/00 |
| | | | 702/56 |
| 2013/0074600 A1 | 3/2013 | Hunter et al. | |
| 2013/0300219 A1 * | 11/2013 | Roberts | H02K 1/34 |
| | | | 310/25 |
| 2014/0103751 A1 * | 4/2014 | Furukawa | H02K 35/02 |
| | | | 310/25 |
| 2014/0150526 A1 | 6/2014 | Powers et al. | |
| 2015/0168208 A1 * | 6/2015 | Sameshima | G01M 5/0008 |
| | | | 73/570 |
| 2015/0253266 A1 | 9/2015 | Lucon et al. | |
| 2015/0268127 A1 | 9/2015 | Berchtold | |
| 2016/0116366 A1 * | 4/2016 | Da Silva | G01N 29/4436 |
| | | | 73/579 |
| 2017/0065154 A1 | 3/2017 | Koshika | |
| 2019/0008388 A1 * | 1/2019 | Ando | G01J 3/00 |
| 2019/0011402 A1 | 1/2019 | Kinoshita et al. | |

FOREIGN PATENT DOCUMENTS

| | | |
|---|---|---|
| JP | H01219555 A | 9/1989 |
| JP | H0471533 A | 3/1992 |
| JP | H08152394 A | 6/1996 |
| JP | 2000314730 A | 11/2000 |
| JP | 2001056319 A | 2/2001 |
| JP | 2004085412 A | 3/2004 |
| JP | 2007198996 A | 8/2007 |
| JP | 2008157945 A | 7/2008 |
| JP | 2009186423 A | 8/2009 |
| JP | 2015111091 A | 6/2015 |
| JP | 2016053548 A | 4/2016 |

OTHER PUBLICATIONS

P. F. d. C. Antunes et al., "Optical Fiber Accelerometer System for Structural Dynamic Monitoring," in IEEE Sensors Journal, vol. 9, No. 11, pp. 1347-1354, Nov. 2009, doi: 10.1109/JSEN.2009.2026548. (Year: 2009).*

Girondin et al., Method for monitoring vibration sensors, EP2728321A1, downloaded from the Espacenet on Apr. 18, 2024 (Year: 2012).*

ISA Japan Patent Office, International Search Report Issued in Application No. PCT/JP2018/013498, Jun. 19, 2018, WIPO, 4 pages.

European Patent Office, Extended European Search Report Issued in Application No. 18791366.0, Dec. 3, 2020, Germany, 10 pages.

* cited by examiner

DETECTION SYSTEM AND DETECTION METHOD

CROSS-REFERENCE TO RELATED APPLICATIONS

The present application is a continuation of U.S. Non-Provisional patent application Ser. No. 16/609,195, entitled "DETECTION SYSTEM AND DETECTION METHOD" and filed Oct. 28, 2019. U.S. Non-Provisional patent application Ser. No. 16/609,195 claims priority to U.S. National Phase of International Patent Application Serial No. PCT/JP2018/013498 entitled "DETECTION SYSTEM AND DETECTION METHOD," filed on Mar. 29, 2018. International Patent Application Serial No. PCT/JP2018/013498 claims priority to Japanese Patent Application No. 2017-090620 filed on Apr. 28, 2017. The entire contents of each of the above-referenced applications are hereby incorporated by reference for all purposes.

TECHNICAL FIELD

The present disclosure generally relates to detection systems and detection methods, in particular to a detection system and a detection method for vibrating an inspection target by applying vibration to the inspection target and detecting a state change of the inspection target by analyzing the vibration of the inspection target.

BACKGROUND

Generally, in order to detect a state change of an inspection target such as a column of a building structure and a concrete structure, there has been used a method of vibrating the inspection target and then detecting and analyzing vibration of the inspection target. When the state change such as a breakdown and a degradation occurs in the inspection target, a resonance (natural) frequency of the vibration of the inspection target changes. Thus, by analyzing the vibration of the inspection target, it is possible to detect the state change of the inspection target.

For example, patent document 1 discloses a frequency measurement device including an excitation unit having an impulse hammer made from a hard material for applying impulse to an inspection target and a sensor for detecting vibration of the inspection target caused by the impulse applied from the excitation unit. When a state of the inspection target changes due to time degradation, breakdown or the like, a mass or a spring constant of the inspection target changes and thus a resonance frequency of the vibration of the inspection target also changes. By using the frequency measurement device disclosed in the patent document 1, it is possible to detect a change in the resonance frequency of the vibration of the inspection target and thereby detect the state change of the inspection target.

However, for vibrating the inspection target with the excitation unit having the impulse hammer as disclosed in the patent document 1, it is necessary to make the excitation unit with an impact-resistant material. Generally, such an impact-resistant material is heavy. Further, since it is necessary to apply big impulse to the inspection target for sufficiently vibrating the inspection target, the impulse hammer itself needs to be big and heavy. This causes a problem that a weight and a size of the frequency measurement device increase.

Further, patent document 2 discloses an abnormality detection system including an excitation unit having an impulse hammer made from a hard material or a piezoelectric element (piezo element) for vibrating an inspection target and a sensor for detecting vibration of the inspection target caused by impulse applied from the impulse hammer or vibration of the piezoelectric element. In a case of vibrating the inspection target with the impulse hammer, the same problem as that of the above-mentioned patent document 1 occurs. On the other hand, in a case of vibrating the inspection target with the piezoelectric element, it is necessary to apply a high input voltage to the piezoelectric element in order to sufficiently vibrate the inspection target. This causes a problem that a power consumption amount required for the abnormality detection system increases.

RELATED ART

Patent Documents

Patent document 1: JP 2008-157945A
Patent document 2: JP 2015-111091A

SUMMARY

Problems to be Solved by the Disclosure

The present disclosure has been made in view of the conventional problems mentioned above. Accordingly, it is an object of the present disclosure to achieve simplification, downsizing and power saving of a detection system which can detect a state change of an inspection target by detecting and analyzing vibration of the inspection target caused by vibration applied to the inspection target.

Means for Solving the Problems

The above object is achieved by the present disclosures defined in the following (1) to (7).
(1) A detection system for detecting a state change of an inspection target, comprising:
  a sensing device including:
    a vibration unit for applying vibration to the inspection target, the vibration unit attached to the inspection target,
    a driving circuit for supplying an electrical signal to the vibration unit for driving the vibration unit, and
    a sensor for detecting vibration of the inspection target caused by the vibration applied from the vibration unit; and
  a detection processing device for receiving vibration information related to the vibration of the inspection target detected by the sensor from the sensing device and detecting the state change of the inspection target based on the vibration information,
  wherein the vibration unit of the sensing device includes a coil in which the electrical signal supplied from the driving circuit flows, a spring provided so as to be capable of vibrating and a magnet attached to the spring so as to be apart from the coil.
(2) The detection system according to the above (1), wherein the detection processing device calculates a resonance frequency of the vibration of the inspection target from the vibration information and detects the state change of the inspection target based on a variation amount of the resonance frequency.
(3) The detection system according to the above (2), wherein the detection processing device includes a storage part for storing the resonance frequency of the vibration of the inspection target, and wherein the detection processing device compares the calculated resonance frequency of the vibration of the inspection target with the resonance frequency of the vibration of the inspection target stored in the storage part in advance to calculate the variation amount of the resonance frequency and detects the state change of the inspection target when the variation amount of the resonance frequency is equal to or more than a predetermined threshold value.

(4) The detection system according to any one of the above (1) to (3), wherein the driving circuit is configured to supply one of an impulse signal, a swept signal and a random signal to the vibration unit as the electrical signal.

(5) The detection system according to any one of the above (1) to (4), wherein the sensor is an acceleration sensor attached to the inspection target or a laser sensor provided so as to be apart from the inspection target.

(6) The detection system according to any one of the above (1) to (5), wherein the detection system contains a plurality of sensing devices, and wherein the detection processing device receives the vibration information related to the vibration of the inspection target from each of the plurality of sensing devices.

(7) A detection method for detecting a state change of an inspection target, comprising:

applying vibration to the inspection target by supplying an electrical signal from a driving circuit to a vibration unit attached to the inspection target to drive the vibration unit;

detecting vibration of the inspection target caused by the vibration applied from the vibration unit by using a sensor; and detecting the state change of the inspection target based on the vibration of the inspection target detected by the sensor by using a processor, wherein the vibration unit includes a coil in which the electrical signal supplied from the driving circuit flows, a spring provided so as to be capable of vibrating and a magnet attached to the spring so as to be apart from the coil.

Effects of the Disclosure

The detection system and the detection method of the present disclosure use a VCM (Voice Coil Motor) type vibration unit as an excitation unit for vibrating an inspection target, which includes a coil in which an electrical signal supplied from a driving circuit flows, a spring provided so as to be capable of vibrating and a magnet attached to the spring so as to be apart from the coil. Thus, it is unnecessary to constitute the vibration unit (the excitation unit) with an impulse-resistant material unlike the conventional art using the impulse hammer. Further, since the VCM type vibration unit can cause big vibration with a relatively low input voltage, it is unnecessary to apply a high input voltage to the vibration unit unlike the conventional art using the piezoelectric element. Thus, according to the present disclosure, it is possible to achieve simplification, downsizing and power saving of the detection system.

DETAILED DESCRIPTION

Hereinafter, description will be given to a detection system and a detection method of the present disclosure based on embodiments shown in the accompanying drawings. First, a detection system according to a first embodiment of the present disclosure will be described in detail with reference to FIGS. 1 to 7.

First Embodiment of Detection System

Figure 1:
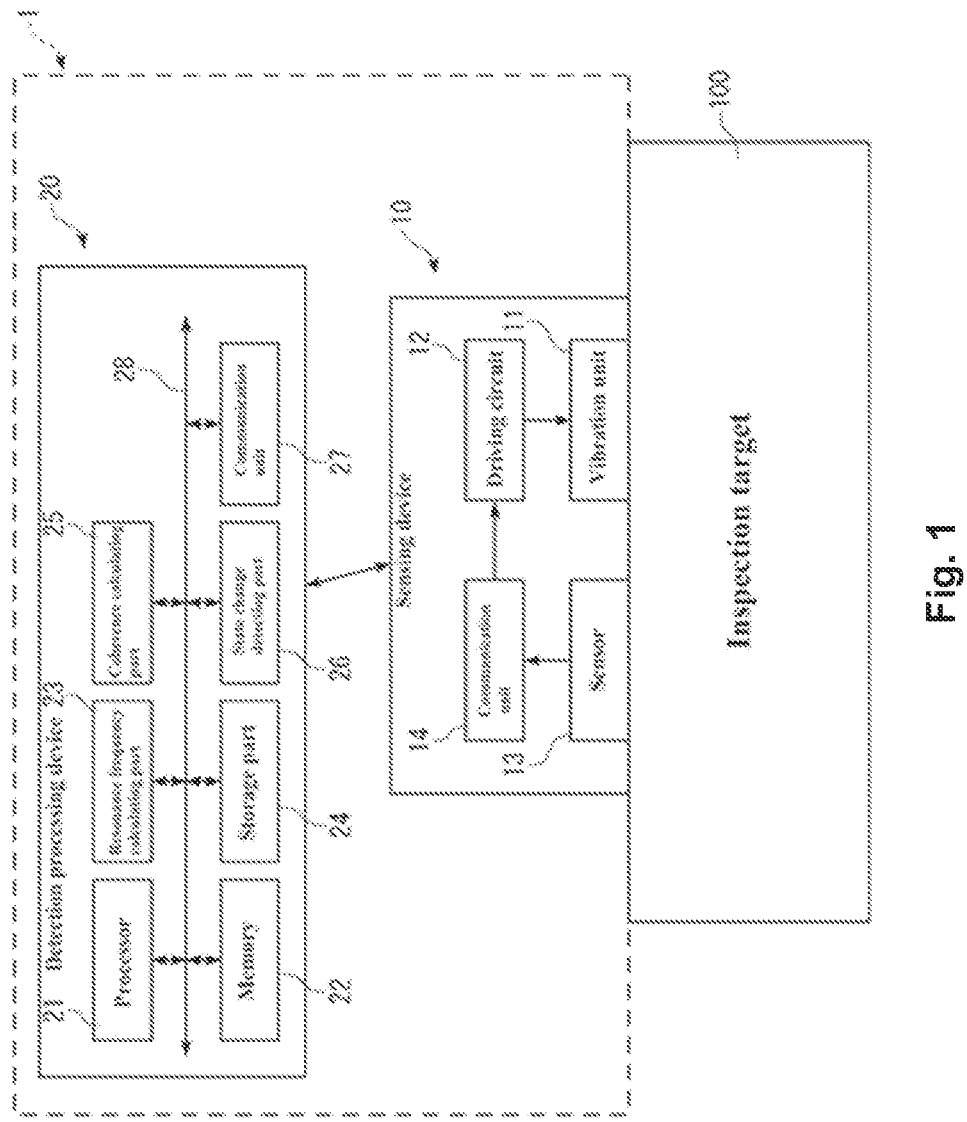
FIG. 1 is a schematic view showing a detection system according to a first embodiment of the present disclosure.
Figure 2:
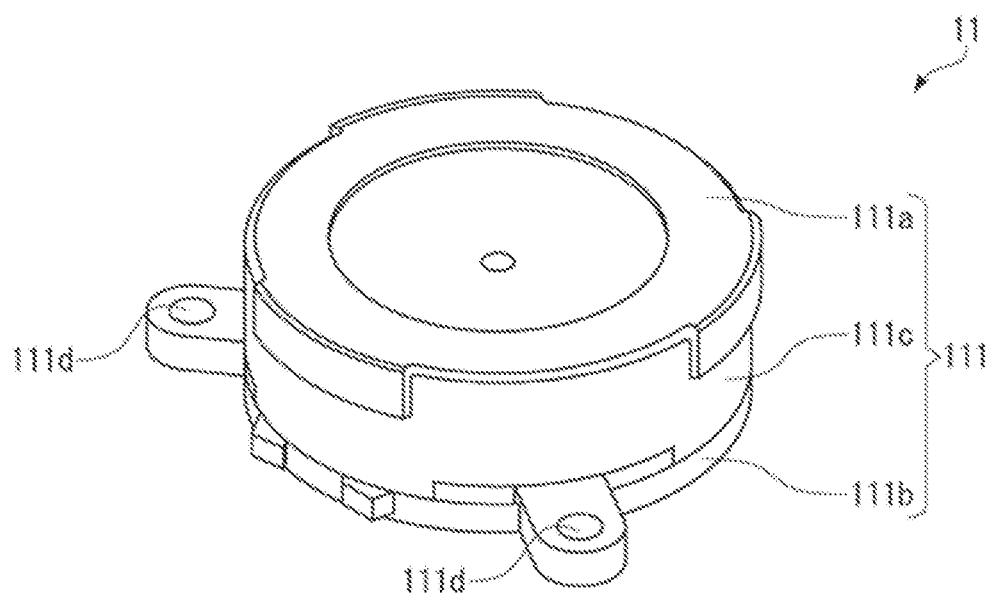
FIG. 2 is a perspective view of a vibration unit shown in FIG. 1.
Figure 3:
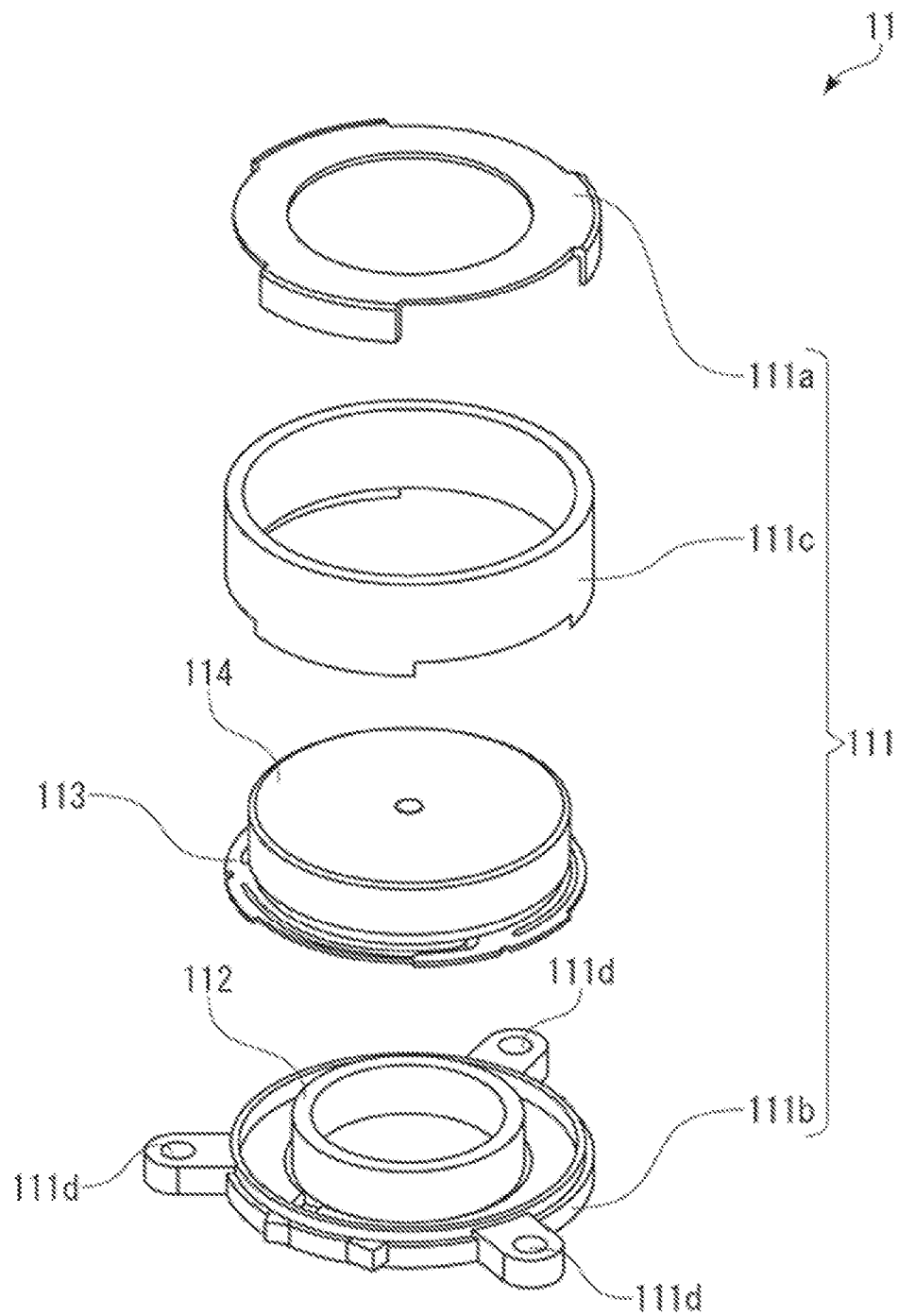
FIG. 3 is an exploded perspective view of the vibration unit shown in FIG. 1.
Figure 4:
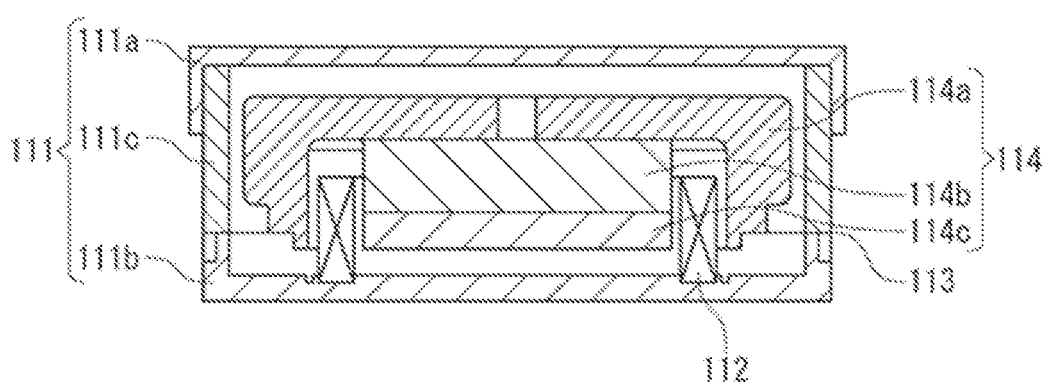
FIG. 4 is a cross-sectional view of the vibration unit shown in FIG. 1.
Figure 5:
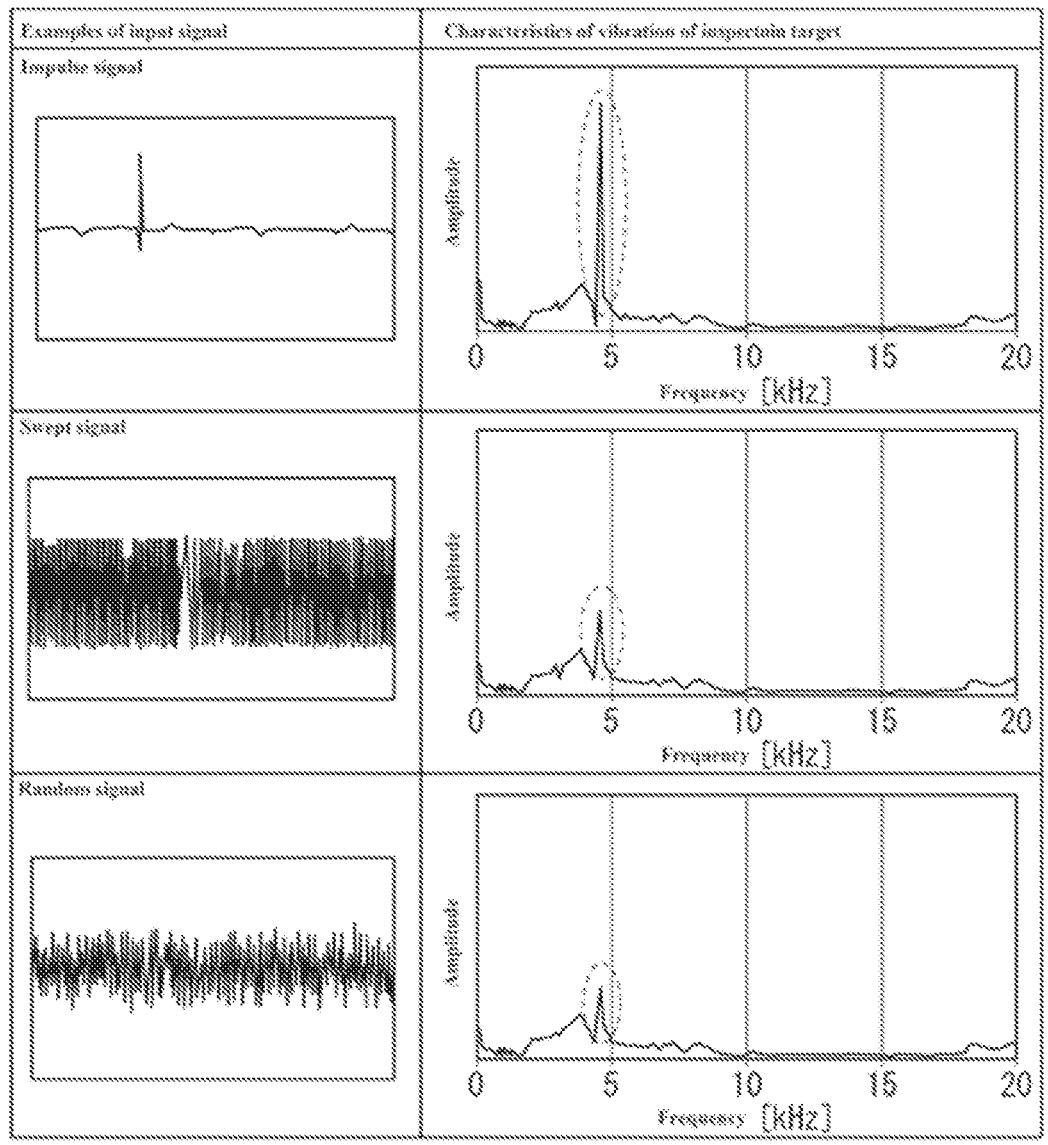
FIG. 5 is a view showing examples of vibration of an inspection target caused when one of an impulse signal, a swept signal and a random signal is supplied to the vibration unit shown in FIG. 1.
Figure 6:
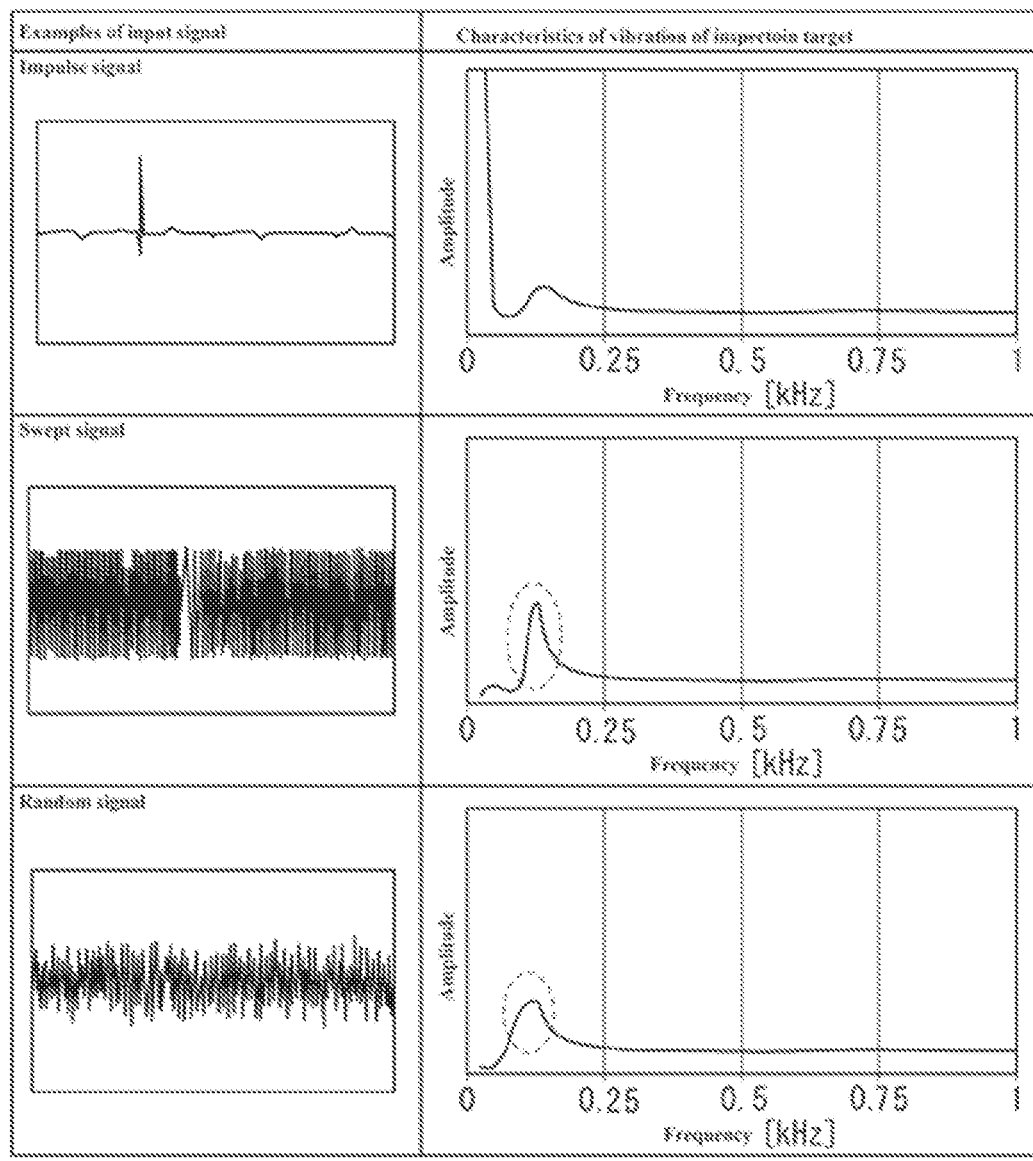
FIG. 6 is a view showing other examples of the vibration of the inspection target caused when one of the impulse signal, the swept signal and the random signal is supplied to the vibration unit shown in FIG. 1.
Figure 7:
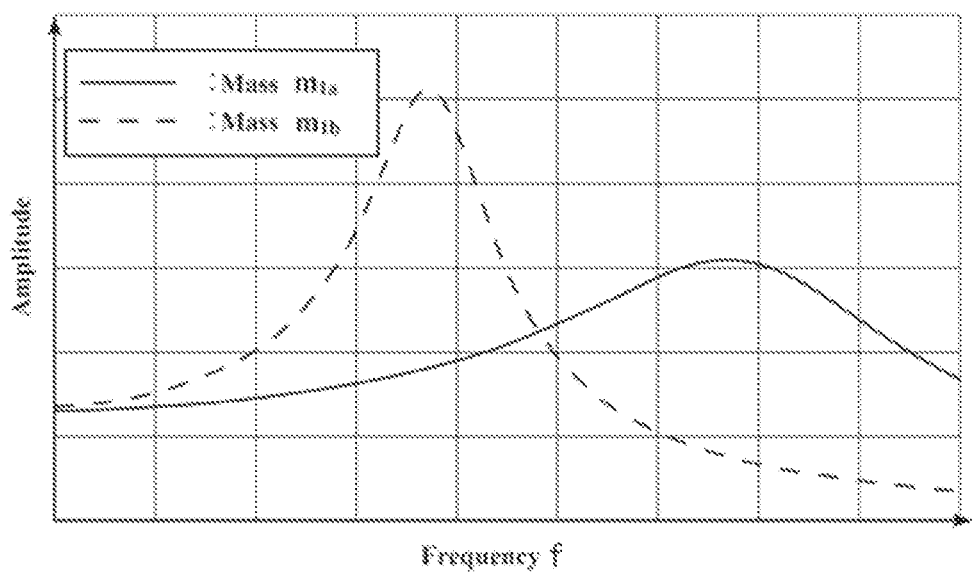
FIG. 7 is a view for explaining a change in characteristics of the vibration of the inspection target caused by a change in a mass of the inspection target shown in FIG. 1.

FIG. 1 is a schematic view showing the detection system according to the first embodiment of the present disclosure. FIG. 2 is a perspective view of a vibration unit shown in FIG. 1. FIG. 3 is an exploded perspective view of the vibration unit shown in FIG. 1. FIG. 4 is a cross-sectional view of the vibration unit shown in FIG. 1. FIG. 5 is a view showing examples of vibration of an inspection target caused when one of an impulse signal, a swept signal and a random signal is supplied to the vibration unit shown in FIG. 1. FIG. 6 is a view showing other examples of the vibration of the inspection target caused when one of the impulse signal, the swept signal and the random signal is supplied to the vibration unit shown in FIG. 1. FIG. 7 is a view for explaining a change in characteristics of the vibration of the inspection target caused by a change in a mass of the inspection target shown in FIG. 1.

A detection system 1 shown in FIG. 1 contains a sensing device 10 for applying vibration to an inspection target 100 and detecting vibration of the inspection target 100 caused by the applied vibration and a detection processing device 20 for detecting a state change of the inspection target 100 based on vibration information related to the vibration of the inspection target 100 received from the sensing device 10.

The sensing device 10 has a function of applying the vibration to the inspection target 100 and detecting the vibration of the inspection target 100 caused by the applied vibration. The sensing device 10 includes a vibration unit 11 attached to the inspection target 100 for applying the vibration to the inspection target 100, a driving circuit 12 for supplying an electrical signal to the vibration unit 11 for driving the vibration unit 11, a sensor 13 for detecting the vibration of the inspection target 100 caused by the vibration applied from the vibration unit 11 and a communication unit 14 for performing communication with the detection processing device 20.

The vibration unit 11 is attached to the inspection target 100 and vibrates according to the electrical signal supplied from the driving circuit 12. The vibration unit 11 is used for applying the vibration to the inspection target 100. As shown in FIGS. 2 to 4, the vibration unit 11 is a VCM (Voice Coil Motor) type vibration unit with a small size (for example, 30 mm height×30 mm vertical width×30 mm horizontal width) and constitutes a single resonance system.

The vibration unit 11 includes a case 111 configured to be attachable to the inspection target 100, a coil 112 fixedly attached on a bottom surface of the case 111 and in which the electrical signal supplied from the driving circuit 12 flows, a spring 113 provided so as to be capable of vibrating with respect to the case 111 and a magnet assembly 114 attached to the spring 113 and provided so as to be apart from the coil 112.

The case 111 is a cylindrical member. The case 111 has functions of fixing the vibration unit 11 to a vibrating body and containing each component of the vibration unit 11 therein. The case 111 includes a cover 111a, a base 111b and a cylindrical portion 111c located between the cover 111a and the base 111b.

Three extending portions are formed on an outer peripheral surface of the base 111b so as to extend in a radial direction of the base 111b and through-holes 111d are respectively formed in tip side portions of the three extending portions. Screws (not shown in the drawings) are respectively passed through the through-holes 111d of the base 111b and respectively screwed with screw holes formed in the inspection target 100. Due to this operation, the base 111b is fixed to the inspection target 100 and thus the vibration unit 11 can be attached (fixed) to the inspection target 100. By attaching the vibration unit 11 to the inspection target 100, it becomes possible to transmit the vibration of the vibration unit 11 to the inspection target 100, thereby vibrating the inspection target 100.

The coil 112 has a cylindrical shape and is fixedly provided on the base 111b. Both end portions (electrical signal supply terminals) of the coil 112 are connected to the driving circuit 12 and thus the electrical signal supplied from the driving circuit 12 flows in the coil 112. Further, as shown in FIG. 4, the coil 112 is located inside a central opening portion of the spring 113 in a state that the vibration unit 11 has been assembled.

The spring 113 has a function of holding the magnet assembly 114 so that the magnet assembly 114 can vibrate with respect to the coil 112. The magnet assembly 114 is attached to the spring 113. When the electrical signal supplied from the driving circuit 12 flows in the coil 112, driving force for moving the magnet assembly 114 attached to the spring 113 in a vertical direction in FIG. 4 occurs. At this time, since the magnet assembly 114 is held by the spring 113 so that the magnet assembly 114 can vibrate with respect to the coil 112, the magnet assembly 114 can vibrate with respect to the coil 112. The spring 113 is not particularly limited as long as it can hold the magnet assembly 114 so that the magnet assembly 114 can vibrate with respect to the coil 112. For example, a leaf spring, a coil spring, a magnetic spring or the like can be used as the spring 113. Hereinafter, for the illustration of the present disclosure, the following description will be given with assuming that the spring 113 is the leaf spring as shown in FIGS. 3 and 4.

The spring 113 has a ring shape with the central opening portion. An outer peripheral portion of the spring 113 is held between the base 111b and the cylindrical portion 111c and a central portion of the spring 113 containing the central opening portion can vibrate with respect to the case 111 in the vertical direction in FIG. 4. The magnet assembly 114 is attached to the central portion of the spring 113 and thus can vibrate with respect to the coil 112.

As shown in FIG. 4, the magnet assembly 114 includes a magnet holding portion 114a having a cylindrical shape opening toward a lower side in FIG. 4, a magnet 114b fixed on a central lower surface of the magnet holding portion 114a and a yoke 114c attached to a lower surface of the magnet 114b.

As shown in FIG. 4, the magnet 114b and the yoke 114c are arranged in a central hollow portion of the coil 112 so as to be apart from the coil 112 in the state that the vibration unit 11 has been assembled. When the electrical signal is supplied to the coil 112 from the driving circuit 12, the driving force for moving the magnet assembly 114 (the magnet 114b) in the vertical direction in FIG. 4. Since the magnet assembly 114 is attached to the spring 113 provided so as to be capable of vibrating, the magnet assembly 114 vibrates in the vertical direction.

As described above, when the electrical signal is supplied to the coil 112 of the vibration unit 11 from the driving circuit 12 and flows in the coil 112, the vibration unit 11 vibrates. A motion equation for representing a motion principle of a single resonance system such as the vibration unit 11 can be represented by the following equation (1).

[Equation 1]

$$m\frac{d^2x(t)}{dt^2} = K_f i(t) - K_{sp}x(t) - D\frac{dx(t)}{dt} \qquad (1)$$

Where, m is a mass [kg], x(t) is a displacement amount [m] of the magnet assembly 114 (vibrator), $K_f$ is a thrust constant [N/A] of the single resonance system, i(t) is a current [A] flowing in the coil 112, $K_{sp}$ is a spring constant [N/m] of the spring 113 and D is a damping coefficient [N/(m/s)] of the single resonance system.

Further, a circuit equation for representing the motion principle of the single resonance system such as the vibration unit 11 can be represented by the following equation (2).

[Equation 2]

$$e(t) = Ri(t) + L\frac{di(t)}{dt} + K_e\frac{dx(t)}{dt} \qquad (2)$$

Where, e(t) is a voltage [V] applied to the coil 112, R is a resistance [Ω] of the coil 112, L is an inductance [H] of the coil 112 and $K_e$ is a counter electromotive force constant [V/(m/s)] of the single resonance system.

From the motion equation and the circuit equation described above, a transfer function G(jω) of the vibration unit 11 represented by the following equation (3) is derived and this transfer function G(jω) indicates specific responses to the electrical signal supplied from the driving circuit 12.

[Equation 3]

$$G(j\omega) = \frac{K_f}{[RK_{sp} - (Rm + DL)\omega^2] + j[(DR + LK_{sp} + K_eK_f)\omega - mL\omega^3]} \quad (3)$$

Namely, a characteristic of the vibration of the vibration unit 11 (output of the single resonance system) changes depending on the kind of the electrical signal supplied to the vibration unit 11 from the driving circuit 12 (input to the single resonance system). For example, FIG. 5 shows examples of the vibration of the inspection target 100 caused when each of an impulse signal, a swept signal and a random signal is supplied to the vibration unit 11 attached to the inspection target 100 for vibrating the vibration unit 11. In this case, a structure constituted of an ABS (Acrylonitrile Butadiene Styrene) resin is used as the inspection target 100. A resonance frequency $f_r$ of the inspection target 100 in this case is in the vicinity of 5 kHz.

As shown in FIG. 5, in all of the cases where any one of the impulse signal, the swept signal and the random signal is supplied to the vibration unit 11, it can be recognized that an amplitude of the vibration of the inspection target 100 maximizes in the vicinity of 5 kHz which is the resonance frequency $f_r$ of the inspection target 100. Thus, in the examples shown in FIG. 5, in all of the cases where any one of the impulse signal, the swept signal and the random signal is supplied to the vibration unit 11, it is possible to detect the resonance frequency $f_r$ of the vibration of the inspection target 100. However, in the examples shown in FIG. 5, when the impulse signal is supplied to the vibration unit 11, the amplitude at the resonance frequency $f_r$ of the inspection target 100 most conspicuously maximizes. This result indicates the fact that to supply the impulse signal to the vibration unit 11 is most suitable for accurately detecting the resonance frequency $f_r$ of the inspection target 100.

On the other hand, FIG. 6 shows other examples of the vibration of the inspection target 100 caused when each of the impulse signal, the swept signal and the random signal is supplied to the vibration unit 11 attached to the inspection target 100 for vibrating the vibration unit 11. In this case, a structure constituted of a plastic material is used as the inspection target 100. The mass and the spring constant of the inspection target 100 in the examples in FIG. 6 are different from the mass and the spring constant of the inspection target 100 in the examples in FIG. 5. The resonance frequency $f_r$ of the inspection target 100 in this case of FIG. 6 is in the vicinity of 0.125 kHz.

As shown in FIG. 6, when the impulse signal is supplied to the vibration unit 11, the amplitude shows a peak in a frequency range other than 0.125 kHz which is the resonance frequency $f_r$ of the inspection target 100. On the other hand, when the swept signal or the random signal is supplied to the vibration unit 11, the amplitude maximizes in the vicinity of 0.125 kHz which is the resonance frequency $f_r$ of the inspection target 100. Thus, in the examples shown in FIG. 6, when the impulse signal is supplied to the vibration unit 11, the resonance frequency $f_r$ of the vibration of the inspection target 100 cannot be accurately detected.

As described above, the kind of the electrical signal which should be supplied to the vibration unit 11 from the driving circuit 12 changes depending on the mass and/or the spring constant of the inspection target 100. Since the driving circuit 12 is configured to supply one of the impulse signal, the swept signal and the random signal to the vibration unit 11 as described later, the sensing device 10 can detect the resonance frequency $f_r$ of the vibration of various kinds of inspection targets 100.

As described above, when the vibration unit 11 attached to the inspection target 100 vibrates, the vibration is applied to the inspection target 100. When the vibration is applied to the inspection target 100 from the vibration unit 11, the vibration of the inspection target 100 is excited. When the inspection target 100 vibrates, the inspection target 100 largely vibrates at the resonance frequency $f_r$ derived from the following equation (4).

[Equation 4]

$$f_r = \frac{1}{2\pi}\sqrt{\frac{K_{sp}}{m_1 + m_2}} \quad (4)$$

Where, $m_1$ is a mass of the inspection target 100, $m_2$ is a mass of the vibration unit 11 attached to the inspection target 100 and $K_{sp}$ is a spring constant of the inspection target 100.

As is clear from the above equation (4), the resonance frequency $f_r$ of the inspection target 100 changes depending on the mass $m_1$ and the spring constant $K_{sp}$ of the inspection target 100. Thus, when a state of the inspection target 100, that is, the mass $m_1$ and the spring constant $K_{sp}$ change due to some factors such as time elapse and breakdown, the resonance frequency $f_r$ of the inspection target 100 also changes.

FIG. 7 shows an example of a change of the resonance frequency $f_r$ of the inspection target 100 when the mass $m_1$ of the inspection target 100 increases from $m_{1a}$ to $m_{1b}$ due to the factors such as time elapse and breakdown. As shown in FIG. 7, when the mass $m_1$ increases from $m_{1a}$ to $m_{1b}$, a frequency at which the amplitude of the vibration of the inspection target 100 maximizes, that is, the resonance frequency $f_r$ is shifted to a lower frequency side. On the other hand, when the mass $m_1$ of the inspection target 100 decreases, the resonance frequency $f_r$ of the inspection target 100 is shifted to a higher frequency side. Similarly, when the spring constant $K_{sp}$ of the inspection target 100 increases, the resonance frequency $f_r$ of the inspection target 100 is shifted to the higher frequency side. When the spring constant $K_{sp}$ of the inspection target 100 decreases, the resonance frequency $f_r$ of the inspection target 100 is shifted to the lower frequency side.

As described above, by detecting the change in the resonance frequency $f_r$ of the inspection target 100, it is possible to detect the change in the mass $m_1$ and/or the spring constant $K_{sp}$ of the inspection target 100, that is the state change of the inspection target 100.

Examples in which the mass $m_1$ of the inspection target 100 decreases due to the factors such as time elapse and breakdown contain a case where the inspection target 100 is a metallic member made from a metallic material such as an iron. When a part of the inspection target 100 falls due to corrosion or weathering with the lapse of time, the mass $m_1$ of the inspection target 100 decreases. On the other hand, examples in which the mass $m_1$ of the inspection target 100 increases due to the factors such as time elapse and breakdown contain a case where the inspection target 100 is arranged outside. When dusts, dirt, sands, water and/or the like are accumulated on the inspection target 100 with the lapse of time, the mass $m_1$ of the inspection target 100 increases.

Examples in which the spring constant $K_{sp}$ of the inspection target 100 changes due to the factors such as time elapse and breakdown contain a case where the inspection target 100 is a structure constituted by coupling a plurality of parts with each other. For example, when bolts or screws for coupling the plurality of parts are loosened or beams among the parts are distorted, the spring constant $K_{sp}$ of the inspection target 100 changes. Further, in a case where the inspection target 100 is a wheel of a tire of a vehicle, the spring constant $K_{sp}$ of the inspection target 100 changes due to loosening of the wheel. Further, in a case where the inspection target 100 is a structure made from a concrete and cracks or breaks occur in the inspection target 100 due to some factors such as time elapse and impulse, the spring constant $K_{sp}$ of the inspection target 100 changes.

As described above, by detecting the change in the resonance frequency $f_r$ of the inspection target 100, it is possible to detect the change in the mass $m_1$ and/or the spring constant $K_{sp}$ of the inspection target 100, that is the state change of the inspection target 100. Thus, the detection system 1 can detect a variety of events such as corrosion or weathering of the inspection target 100, increase of an accumulated material on the inspection target 100, loosening of the bolts or the screws of the inspection target 100, distortion of the beam of the inspection target 100, loosening of the wheel of the inspection target 100 and occurrence of the cracks or the breaks of the inspection target 100.

Referring back to FIG. 1, the driving circuit 12 has a function of supplying the electrical signal to the vibration unit 11 for driving (vibrating) the vibration unit 11. The driving circuit 12 is configured to supply at least one of the impulse signal, the swept signal and the random signal to the vibration unit 11 according to control data received from the detecting processing device 20 through the communication unit 14.

The sensor 13 has a function of detecting the vibration of the inspection target 100 caused by the vibration applied from the vibration unit 11. Vibration information related to the vibration of the inspection target 100 detected by the sensor 13 is transmitted to the detection processing device 20 through the communication unit 14. For example, the vibration information transmitted to the detection processing device 20 from the sensor 13 is an acceleration or the like of the vibration (motion) of the inspection target 100. By performing a process such as a Fourier transformation with respect to the vibration information, it is possible to obtain amplitudes (energies) at respective frequencies of the vibration of the inspection target 100.

The sensor 13 is not particularly limited as long as it can detect the vibration of the inspection target 100. For example, it is possible to use an acceleration sensor attached to the inspection target 100 for detecting an acceleration of the motion of the inspection target 100, a laser sensor provided so as to be apart from the inspection target 100 for irradiating laser to the inspection target 100 and detecting the motion of the inspection target 100 based on the laser reflected from the inspection target 100 or the like as the sensor 13.

The communication unit 14 has a function of communicating with the detection processing device 20 to receive the control data from the detection processing device 20 and transmitting the vibration information related to the vibration of the inspection target 100 detected by the sensor 13 to the detection processing device 20. In a case where the sensing device 13 is connected to the detecting processing device 20 with a wired connection, the communication unit 14 performs communication with the detection processing device 20 with wired communication. In a case where the sensing device 13 is not connected to the detecting processing device 20 with the wired connection, the communication unit 14 performs communication with the detection processing device 20 with a wireless communication technology such as an NFC (Near Field Radio Communication), a Wi-Fi and a Bluetooth (registered trademark).

In this regard, power supply to each component of the sensing device 10 may be achieved by an internal power source such as a battery build in the sensing device 10 or an external power source arranged outside the sensing device 10 and connected to the sensing device 10 with a power supply wire.

The detection processing device 20 has functions of transmitting the control data to the sensing device 10, receiving the vibration information related to the vibration of the inspection target 100 detected by the sensor 13 from the sensing device 10 and detecting the state change of the inspection target 100 based on the received vibration information.

The detection processing device 20 may be practiced as a stand-alone device or practiced in an arbitrary computing device such as a desktop computer, a laptop computer, a notebook computer, a workstation, a tablet computer, a mobile phone, a smart phone, a PDA and a wearable device.

The detection processing device 20 includes at least one processor 21 for performing control for the detection processing device 20, a memory 22 storing data, programs, modules and the like required for performing the control of the detection processing device 20, a resonance frequency calculating part 23 for calculating the resonance frequency $f_r$ of the vibration of the inspection target 100 based on the received vibration information, a storage part 24 for storing the resonance frequency $f_r$ calculated by the resonance frequency calculating part 23 and/or a reference resonance frequency $f_{ref}$ of the vibration of the inspection target 100, a coherence calculating part 25 for calculating a coherence $\gamma^2$ between the vibration of the vibration unit 11 of the sensing device 10 and the vibration of the inspection target 100, a state change detecting part 26 for detecting the state change of the inspection target 100 by comparing the resonance frequency $f_r$ of the vibration of the inspection target 100 calculated by the resonance frequency calculating part 23 with the reference resonance frequency $f_{ref}$ stored in the storage part 24 or a previous resonance frequency $f_r$ of the vibration of the inspection target 100 stored in the storage part 24, a communication unit 27 for performing communication with the sensing device 10 and a data bus 28 for transmitting and receiving data between respective components of the detection processing device 20.

The processor 21 performs, transmits and receives a variety of data or a variety of instructions with each component through the data bus 28 for performing the control of the detection processing device 20. Further, the processor 21 can provide desired functions by using each component of the detection processing device 20. For example, the processor 21 can use the resonance frequency calculating part 23 to calculate the resonance frequency $f_r$ of the vibration of the inspection target 100 based on the received vibration information, use the coherence calculating part 25 to calculate the coherence $\gamma^2$ between the vibration of the vibration unit 11 of the sensing device 10 and the vibration of the inspection target 100 and use the state change detecting part 26 to detect the state change of the inspection target 100.

Further, the processor 21 transmits the control data to the sensing device 10 through the communication unit 27 at prescribed time intervals (such as every hour, every day, every week and every week) for allowing the sensing device 10 to measure the vibration of the inspection target 100. The control data transmitted from the processor 21 is used for identifying which one of the impulse signal, the swept signal and the random signal should be supplied to the vibrating unit 11 from the driving circuit 12 of the sensing device 10. The driving circuit 12 receiving the control data supplies one of the impulse signal, the swept signal and the random signal to the vibration unit 11 according to the control data for vibrating the vibration unit 11.

The processor 21 is one or more operation units such as microprocessors, microcomputers, microcontrollers, digital signal processors (DSPs), central processing units (CPUs), memory control units (MCUs), graphic processing units (GPUs), state machines, logic circuitries, application specific integrated circuits (ASICs) and combinations thereof that can perform operational processes for manipulating signals or the like based on computer-readable instructions. Among other capabilities, the processor 21 is configured to fetch computer-readable instructions (such as data, programs and modules) stored in the memory 22 and execute signal control and signal manipulation.

The memory 22 is one or more removable or non-removable computer-readable media including volatile memories (such as RAMs, SRAMs and DRAMs), non-volatile memories (such as ROMs, EPROMs, EEPROMs, flash memories, hard disks, optical discs, CD-ROMs, digital versatile discs (DVDs), magnetic cassettes, magnetic tapes and magnetic disks) and combinations thereof.

The resonance frequency calculating part 23 has a function of calculating the resonance frequency $f_r$ of the vibration of the inspection target 100 based on the vibration information received from the sensing device 10 through the communication unit 27. Specifically, the resonance frequency calculating part 23 performs the process such as a Fourier transformation with respect to the received vibration information to calculate the amplitudes (energies) at the respective frequencies of the vibration of the inspection target 100 as shown in FIG. 7. The resonance frequency calculating part 23 identifies a frequency having the largest amplitude (energy) as the resonance frequency $f_r$ of the vibration of the inspection target 100.

The storage part 24 is an arbitrary non-volatile storage media (such as a hard disk and a flash memory) for storing the resonance frequency $f_r$ calculated by the resonance frequency calculating part 23 and/or the reference resonance frequency $f_{ref}$ of the vibration of the inspection target 100. The reference resonance frequency $f_{ref}$ of the vibration of the inspection target 100 is a resonance frequency $f_r$ of the vibration of the inspection target 100 when the inspection target 100 is in a normal state. The reference resonance frequency $f_{ref}$ is measured and stored in the storage part 24 before the detection system 1 starts to operate. Further, the resonance frequency $f_r$ of the vibration of the inspection target 100 calculated by the resonance frequency calculating part 23 is stored in storage part 24 as accumulated data every time when the resonance frequency calculating part 23 calculates the resonance frequency $f_r$. Such accumulated data can be used for tracking the state change of the inspection target 100 in time series to provide information useful for maintenance and inspection of the inspection target 100. Further, such accumulated data may be transmitted to a manager or the like for the inspection target 100 as a report at prescribed time intervals (such as every hour, every day, every week and every month).

The storage part 24 further stores vibration information related to the vibration of the vibration unit 11 obtained in advance. The vibration information related to the vibration of the vibration unit 11 contains at least vibration information related to the vibration of the vibration unit 11 caused when the driving circuit 12 supplies the impulse signal to the vibration unit 11, vibration information related to the vibration of the vibration unit 11 caused when the driving circuit 12 supplies the swept signal to the vibration unit 11 and vibration information related to the vibration of the vibration unit 11 caused when the driving circuit 12 supplies the random signal to the vibration unit 11. The vibration information related to the vibration of the vibration unit 11 as described above is used for allowing the coherence calculating part 25 described later to calculate the coherence $\gamma^2$ between the vibration of the vibration unit 11 of the sensing device 10 and the vibration of the inspection target 100.

The coherence calculating part 25 has a function of calculating the coherence $\gamma^2$ between the vibration of the vibration unit 11 of the sensing device 10 and the vibration of the inspection target 100 based on the vibration information related to the vibration of the vibration unit 11 of the sensing device 10 stored in the storage part 24 and the vibration information related to the vibration of the inspection target 100 received from the sensing device 10. Specifically, the coherence calculating part 25 uses the following equation (5) to calculate a coherence value between the vibration of the vibration unit 11 of the sensing device 10 and the vibration of the inspection target 100.

[Equation 5]

$$\gamma^2 = \frac{|W_{xy}|^2}{W_{xx} \cdot W_{yy}} \quad (5)$$

Where, $W_{xx}$ is a power spectrum of an input vibration, that is a power spectrum of the vibration of the vibration unit 11. $W_{xx}$ is calculated from the vibration information related to the vibration of the vibration unit 11 of the sensing device 10 stored in the storage part 24. $W_{yy}$ is a power spectrum of an output vibration, that is a power spectrum of the vibration of the inspection target 100. $W_{xy}$ is a cross spectrum between the vibration of the vibration unit 11 and the vibration of the inspection target 100.

The coherence $\gamma^2$ described above represents a strength of a relationship between the input vibration and the output vibration. By referring to the value of the coherence $\gamma^2$ described above, it is possible to determine whether or not resonance of the inspection target 100 is excited by the vibration of the vibration unit 11. As the coherence $\gamma^2$ approaches 1, this result indicates that the resonance of the inspection target 100 is efficiently excited by the vibration of the vibration unit 11. As the coherence $\gamma^2$ approaches 0, this result indicates that the resonance of the inspection target 100 is not excited by the vibration of the vibration unit 11.

When the coherence $\gamma^2$ described above becomes less than 0.5, this result indicates that the inspection target 100 is not sufficiently resonated (vibrated). As described above, by referring to the coherence $\gamma^2$ calculated by the coherence calculating part 25, it is possible to determine whether or not the inspection target 100 is sufficiently vibrated. The processor 21 changes the control data depending on the value of the coherence $\gamma^2$ calculated by the coherence calculating part 25. For example, if the coherence $\gamma^2$ is less than 0.5 when the impulse signal is supplied from the driving circuit 12 to the vibration unit 11, the processor 21 interprets that the resonance of the inspection target 100 is not excited by supplying the impulse signal to the vibration unit 11. After that, the processor 21 changes the control data so that the swept signal or the random signal is supplied to the vibration unit 11 from the driving circuit 12 and transmits the changed control data to the driving circuit 12 through the communication unit 27.

The state change detecting part 26 has a function of detecting the state change of the inspection target 100 by comparing the resonance frequency $f_r$ of the vibration of the inspection target 100 calculated by the resonance frequency calculating part 23 with the reference resonance frequency $f_{ref}$ stored in the storage part 24 or the previous resonance frequency $f_r$ of the vibration of the inspection target 100 stored in the storage part 24. Specifically, the state change detecting part 26 calculates a difference between the resonance frequency $f_r$ of the vibration of the inspection target 100 calculated by the resonance frequency calculating part 23 and the reference resonance frequency $f_{ref}$ or the previous resonance frequency $f_r$ of the vibration of the inspection target 100 stored in the storage part 24 and then determines whether or not an absolute value of the calculated difference, that is, a variation amount of the resonance frequency $f_r$ is equal to or more than a predetermined threshold value. The predetermined value is appropriately set depending on some factors such as a size, a constituent material, a shape or the like of the inspection target 100.

In a case of determining that the absolute value of the calculated difference (the variation amount of the resonance frequency $f_r$) is equal to or more than the predetermined threshold value, the state change detecting part 26 detects the state change of the inspection target 100. On the other hand, in a case of determining that the absolute value of the calculated difference (the variation amount of the resonance frequency $f_r$) is less than the predetermined threshold value, the state change detecting part 26 detects that the state change of the inspection target 100 does not occur. After that, the processor 21 performs a process according to a result of the detection by the state change detecting part 26. For example, the processor 21 performs a process for transmitting a message indicating that the state change of the inspection target 100 is detected to a user device (such as a desktop computer, a laptop computer, a notebook computer, a workstation, a tablet computer, a mobile phone, a smart phone, a PDA and a wearable device) of the manager or the like for the inspection target 100 when the state change of the inspection target 100 is detected. With this configuration, the manager or the like for the inspection target 100 can know occurrence of the state change of the inspection target 100 and take an appropriate response.

The communication unit 27 has a function of performing the communication with the sensing device 10 to transmit the control data to the sensing device 10 and receive the vibration information related to the vibration of the inspection target 100 detected by the sensor 13 of the sensing device 10 from the sensing device 10. Further, the communication unit 27 has a function of performing communication with the user device of the manager for the inspection target 100. The manager for the inspection target 100 performs the communication with the detection processing device 20 through the communication unit 27 to change various setting of the detection processing device 20 (such as setting of time intervals (every day, every week or the like) with which the detection process should be performed). Further, the detection processing device 20 can transmit the above-mentioned accumulated data or the message to the user device of the manager for the inspection target 100 through the communication unit 27. As is the case of the communication unit 14, the communication unit 27 can use a variety of wired communication and wireless communication to perform the communication with the sensing device 10 or the user device of the manager for the inspection target 100. Further, the communication unit 27 may use a variety of wired communication and wireless communication to perform communication with a variety of external devices other than the sensing device 10 or the user device of the manager for the inspection target 100.

In this regard, power supply to each component of the detection processing device 20 may be achieved by an internal power source such as a battery build in the detection processing device 20 or an external power source arranged outside the detection processing device 20 and connected to the detection processing device 20 with a power supply wire.

As described above, the detection system 1 of the present disclosure 1 uses the VCM type vibration unit 11 including the coil 112 in which the electrical signal supplied from the driving circuit 12 for applying the vibration to the inspection target 100 flows, the spring 113 provided so as to be capable of vibrating and the magnet 114b attached to the spring 113 so as to be apart from the coil 112. Thus, it is unnecessary to constitute the vibration unit 11 with an impulse-resistant material unlike the conventional art using the impulse hammer. Further, since the VCM type vibration unit 11 can cause big vibration with a relatively low input voltage, it is unnecessary to apply a high input voltage to the vibration unit 11 unlike the conventional art using the piezoelectric element. Thus, according to the present disclosure, it is possible to achieve simplification, downsizing and power saving of the detection system 1.

In this regard, although the sensing device 10 and the detection processing device 20 are described as separated devices respectively contained in different cases in this embodiment, the present disclosure is not limited thereto. For example, a unit for providing functions equivalent to the functions of the sensing device 10 and a unit for providing functions equivalent to the detection processing device 20 may be contained in one case and practiced as one device.

Second Embodiment of Detection System

Figure 8:
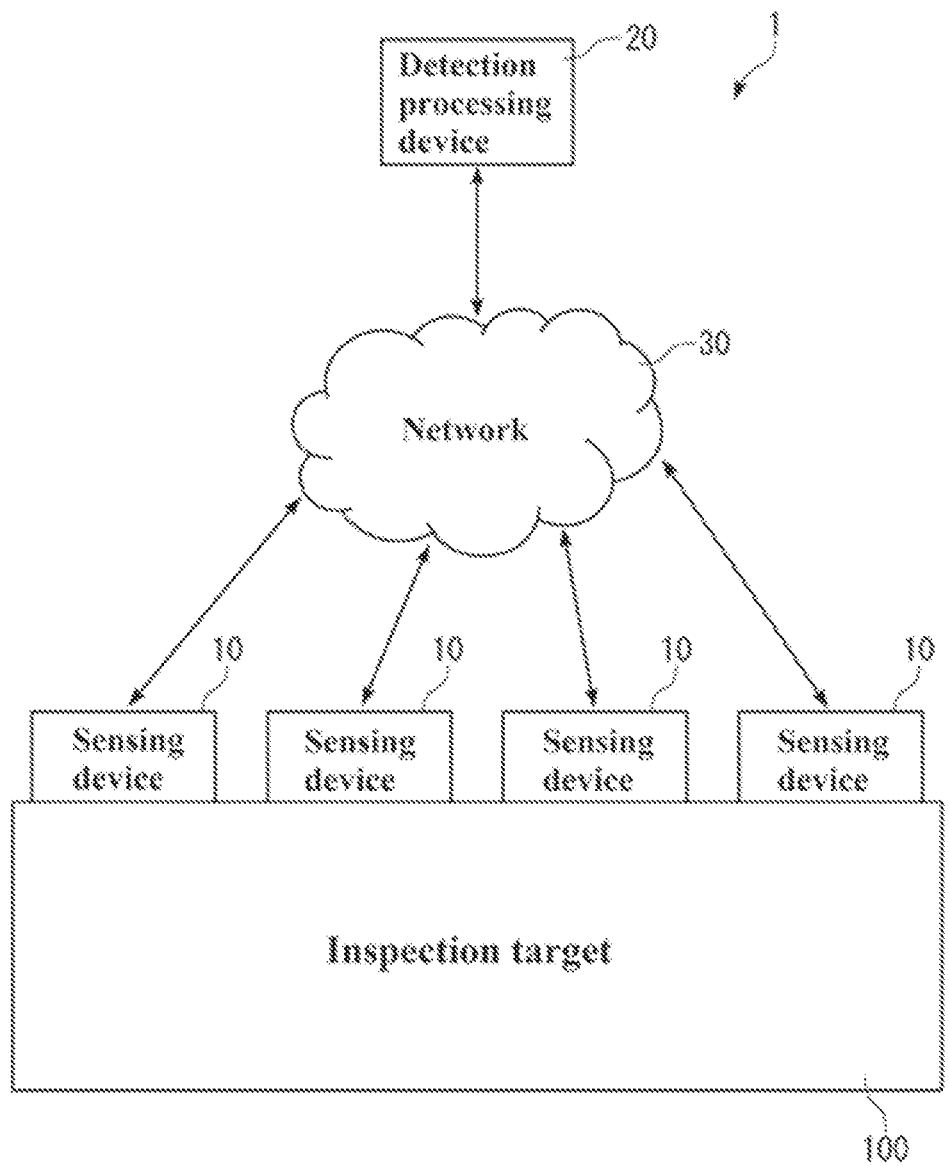
FIG. 8 is a schematic view showing a detection system according to a second embodiment of the present disclosure.

Next, description will be given to a detection system according to a second embodiment of the present disclosure with reference to FIG. 8. FIG. 8 is a schematic view showing the detection system according to the second embodiment of the present disclosure. Hereinafter, the detection system of the second embodiment will be described by placing emphasis on the points differing from the detection system of the first embodiment, with the same matters being omitted from the description.

A detection system 1 of the second embodiment is the same as the detection system 1 of the first embodiment except that the detection system 1 contains a plurality of sensing devices 10 and the detection processing device 20 are communicatively connected to the plurality of sensing devices 10 through a network 30.

The detection processing device 20 in this embodiment may be a stand-alone device connected to the network 30 or practiced in a server connected to the network 30.

The plurality of sensing devices 10 in this embodiment are attached to one inspection target 100. The plurality of sensing devices 10 are communicatively connected to the detection processing device 20 through the network 30.

The network 30 is a variety of networks such as an intranet, a local area network (LAN), a wide area network (WAN), Internet and combinations thereof. Further, the network 30 may be a dedicated network or a shared network. The shared network represents an association of the different types of networks that use a variety of protocols (such as HTTP, TCP/IP and WAP) to communicate with each other. Further the network 30 may include a variety of network devices, including routers, bridges, servers, computing devices, storage devices and the like.

The detection processing device 20 receives the vibration information of the vibration of the inspection target 100 from the plurality of sensing devices 10 through the network 30. With this configuration, it becomes possible to detect the presence or absence of the state changes of locations of the inspection target 100 to which the plurality of sensing devices 10 are respectively attached and detect the presence or absence of the state change of the whole of the inspection target 100. The detection system 1 with the above-mentioned aspect is especially useful to a case where the inspection target 100 is a large size structure such as a bridge and a tunnel.

Third Embodiment of Detection System

Figure 9:
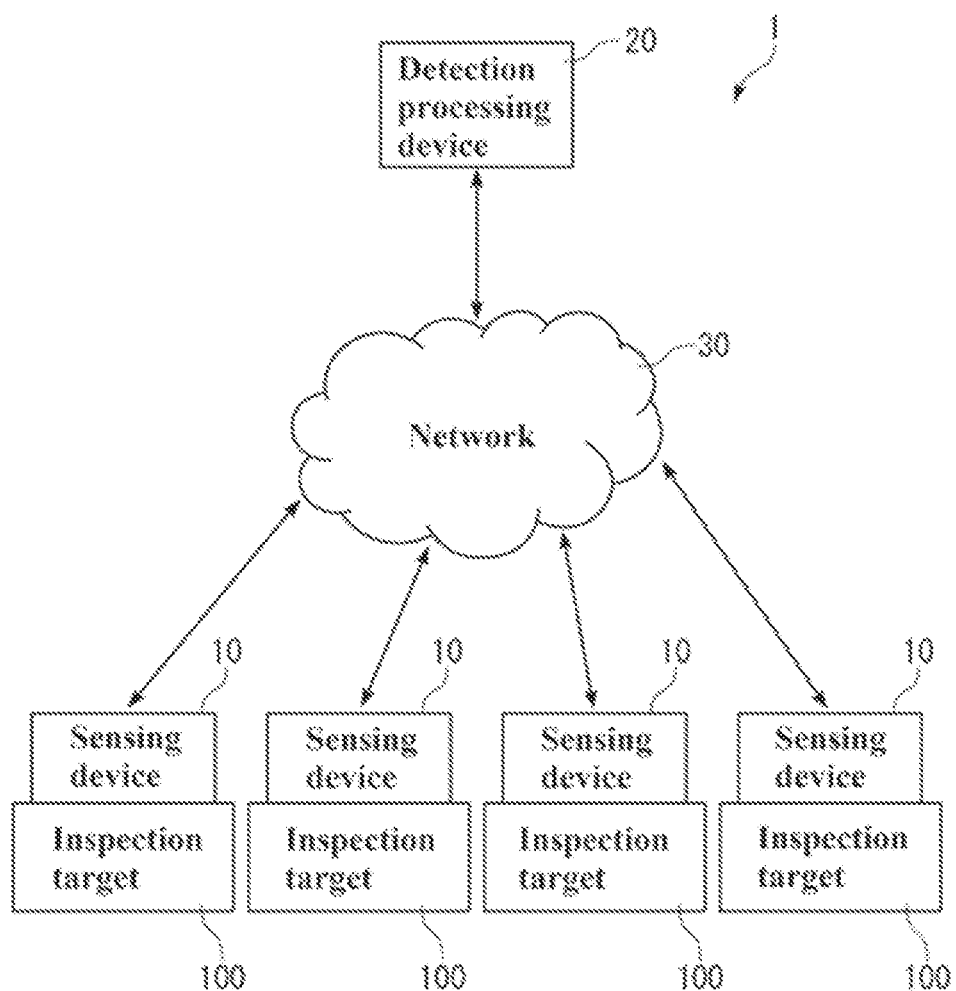
FIG. 9 is a schematic view showing a detection system according to a third embodiment of the present disclosure.

Next, description will be given to a detection system according to a third embodiment of the present disclosure with reference to FIG. 9. FIG. 9 is a schematic view showing the detection system according to the third embodiment of the present disclosure. Hereinafter, the detection system of the third embodiment will be described by placing emphasis on the points differing from the detection system of the second embodiment, with the same matters being omitted from the description.

A detection system 1 of the third embodiment is the same as the detection system 1 of the second embodiment except that the plurality of sensing devices 10 are respectively attached to different inspection targets 100.

In the detection system 1 of this embodiment, the plurality of sensing devices 10 are respectively attached to the different inspection targets 100. The detection system 1 with this aspect is especially useful for a case where the plurality of inspection targets 100 having relatively small sizes are arranged so as to be apart from each other.

Detection Method

Figure 10:
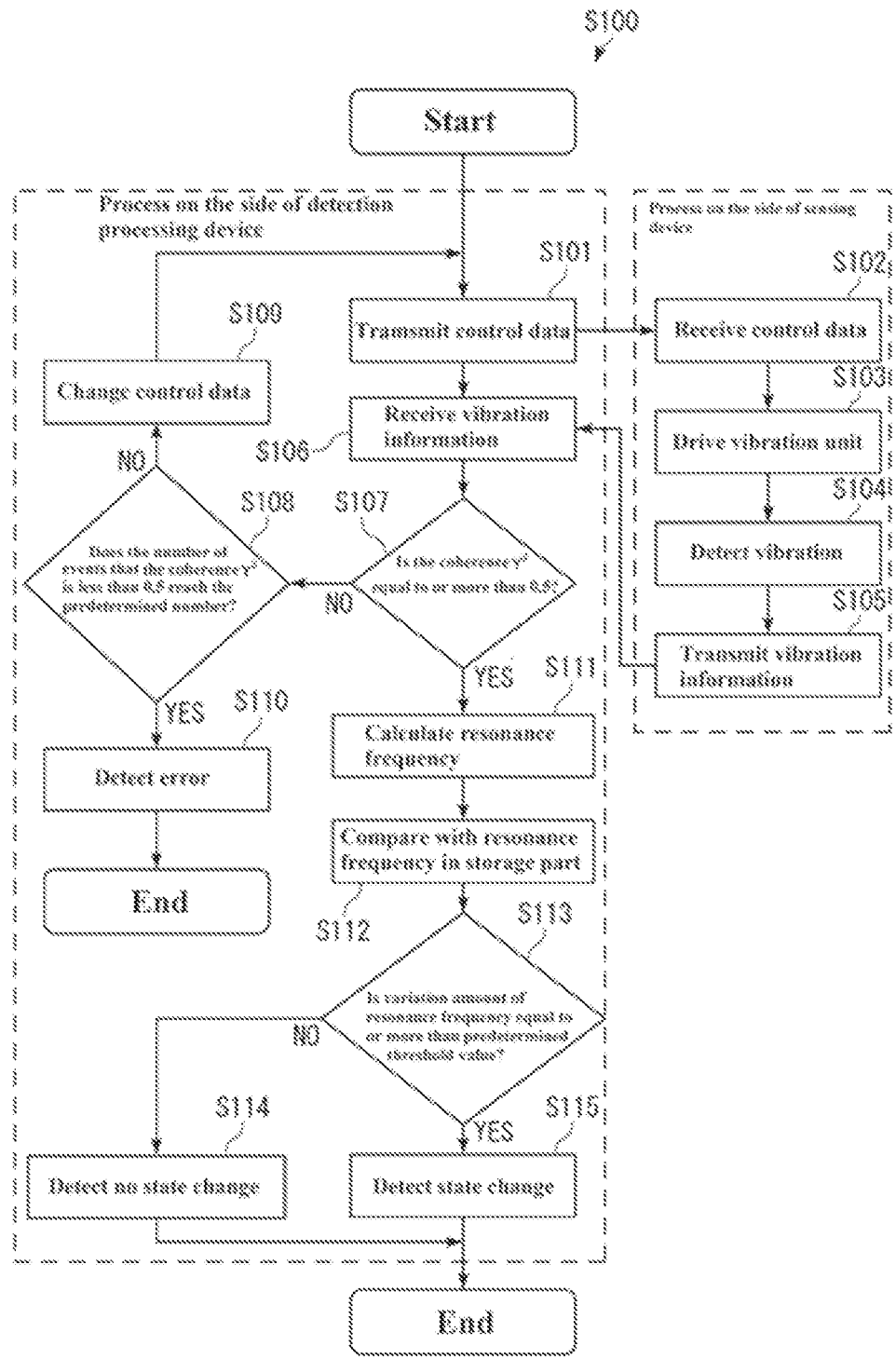
FIG. 10 is a flow chart showing a detection method of the present disclosure.

Next, description will be given to a detection method of the present disclosure with reference to FIG. 10. In this regard, although the detection method of the present disclosure can be performed with the detection system 1 of the present disclosure or an arbitrary system having a function equivalent to the function of the detection system 1 of the present disclosure, the following description will be given with assuming that the detection method of the present v is performed with the detection system 1. FIG. 10 is a flow chart showing the detection method of the present disclosure.

A detection method S100 of the present disclosure is performed at prescribed time intervals (such as every hour, every day, every week and every month). At a step S101, the control data is created by the processor 21 of the detection processing device 20 and the created control data is transmitted to the sensing device(s) 10 through the communication unit 27. The created and transmitted control data is used for identifying which one of the impulse signal, the swept signal and the random signal should be supplied to the vibration unit 11 from the driving circuit 12 in the sensing device 10.

At a step S102, the control data is received by the communication unit 14 of the sensing device 10 and transmitted to the driving circuit 12. The driving circuit 12 supplies one of the impulse signal, the swept signal and the random signal to the vibration unit 11 according to the control data. Next, at a step S103, the vibration unit 11 is driven by the electrical signal supplied from the driving circuit 12 and the vibration unit 11 vibrates. When the vibration unit 11 vibrates, the vibration of the vibration unit 11 is applied to the inspection target 100 and thereby the inspection target 100 vibrates.

Next, at a step S104, the sensor 13 detects the vibration of the inspection target 100. At a step S105, the sensor 13 transmits the vibration information related to the detected vibration of the inspection target 100 to the detection processing device 20 through the communication unit 14. As a step S106, the detection processing device 20 receives the vibration information related to the vibration of the inspection target 100 through the communication unit 27.

At a step S107, the processor 21 of the detection processing device 20 uses the coherence calculating part 25 to calculate the coherence $\gamma^2$ between the vibration of the vibration unit 11 of the sensing device 10 and the vibration of the inspection target 100. The coherence $\gamma^2$ is calculated based on the received vibration information related to the vibration of the inspection target 100 and the vibration information related to the vibration of the vibration unit 11 stored in the storage part 24. In this regard, the vibration information related to the vibration of the vibration unit 11 used in this step corresponds to the vibration caused when the kind of the electrical signal identified by the control data is supplied to the vibration unit 11. For example, when the kind of the electrical signal identified by the control data is the impulse signal, the vibration information related to the vibration of the vibration unit 11 caused when the impulse signal is supplied to the vibration unit 11 among the vibration information stored in the storage part 24 is used at the step S107.

The processor 21 determines whether or not the calculated coherence $\gamma^2$ is equal to or more than 0.5. In the case of determining that the calculated coherence $\gamma^2$ is less than 0.5, the processor 21 determines that the vibration (resonance) of the inspection target 100 is not sufficiently excited by the vibration of the vibration unit 11 and then the process is shifted to a step S108. At the step S108, the processor 21 determines whether or not the number of the events that the coherence $\gamma^2$ is less than 0.5 reaches a predetermined number. Here, the predetermined number corresponds to the number of the kinds of the electrical signals which can be supplied to the vibration unit 11 from the driving circuit 12. For example, in the case where the driving circuit 12 is configured to be capable of supplying the three kinds of the electrical signals, that is the impulse signal, the swept signal and the random signal, the predetermined number is three.

In a case of determining that the number of the events that the coherence $\gamma^2$ is less than 0.5 does not reach the predetermined number, the process is shifted to a step S109. At the step S109, the processor 21 changes the control data to change the kind of the electrical signal to be supplied to the vibration unit 11 from the driving circuit 12 to the kind which has not yet been supplied to the vibration unit 11. For example, when the impulse signal has been already supplied to the vibration unit 11, the kind of the electrical signal to be supplied to the vibration unit 11 from the driving circuit 12 is changed to the swept signal or the random signal. After that, the process returns to the step S101.

On the other hand, in a case of determining that the number of the events that the coherence $\gamma^2$ is less than 0.5 reaches the predetermined number at the step S108, the process is shifted to a step S110. The fact that the number of the events that the coherence $\gamma^2$ is less than 0.5 reaches the predetermined number represents that the vibration of the vibration unit 11 caused by all of the electrical signals which can be supplied to the vibration unit 11 from the driving circuit 12 can not sufficiently excite the vibration (resonance) of the inspection target 100. In this case, there is a high possibility that some sort of trouble occurs in the sensing device 10. For example, it is expected that some sort of trouble that the sensing unit 11 is detached from the inspection target 100, the vibration unit 11 or the sensor 13 gets out of order or sufficient power is not supplied to the sensing device 10 occurs. Thus, at a step S110, the processor 21 transmits an error message indicating that an error is detected to the user device of the manager or the like for the inspection target 100 through the communication unit 27 and then the process finishes. By transmitting such an error message to the user device of the manager or the like for the inspection target 100, the manager or the like for the inspection target 100 can take an appropriate response. For example, the manager or the like can confirm a state of the sensing device 10 or the like.

On the other hand, in a case of determining that the coherence $\gamma^2$ is equal to or more than 0.5, the process is shifted to a step S111. At the step S111, the processor 21 uses the resonance frequency calculating part 23 to calculate the resonance frequency $f_r$ of the vibration of the inspection target 100 based on the vibration information related to the vibration of the inspection target 100. The calculated resonance frequency $f_r$ of the vibration of the inspection target 100 is stored in the storage part 24 as the current resonance frequency $f_r$ of the vibration of the inspection target 100.

At a step S112, the processor 21 uses the state change detecting part 26 to compare the current resonance frequency $f_r$ of the vibration of the inspection target 100 calculated by the resonance frequency calculating part 23 with the previous resonance frequency $f_r$ of the vibration of the inspection target 100 stored in the storage part 24 or the reference resonance frequency $f_{ref}$ stored in the storage part 24 to calculate the difference between the current resonance frequency $f_r$ calculated by the resonance frequency calculating part 23 and the previous resonance frequency $f_r$ or the reference resonance frequency $f_{ref}$ stored in the storage part 24.

At a step S113, it is determined whether or not the absolute value of the difference between the current resonance frequency $f_r$ calculated by the resonance frequency calculating part 23 and the previous resonance frequency $f_r$ or the reference resonance frequency $f_{ref}$ stored in the storage part 24, that is, the variation amount of the resonance frequency $f_r$ is equal to or more than the predetermined threshold value. In a case of determining that the absolute value of the calculated difference (the variation amount of the resonance frequency $f_r$) is less than the predetermined threshold value at the step S113, the process is shifted to a step S114. At the step S114, it is detected that the state change of the inspection target 100 does not occur and the processor 21 performs the process according to the detection result. After that, the detection method S100 finishes.

On the other hand, in a case of determining that the absolute value of the calculated difference (the variation amount of the resonance frequency $f_r$) is equal to or more than the predetermined threshold value at the step S113, the process is shifted to a step S115. At the step S115, it is detected that the state change of the inspection target 100 occurs and the processor 21 performs the process according to the detection result. After that, the detection method S100 finishes.

Although the detection system 1 and the detection method S100 of the present disclosure have been described based on the embodiments shown in the accompanying drawings in the above description, the present disclosure is not limited thereto. The configuration of each component of the present disclosure may be possibly replaced with other arbitrary configurations having equivalent functions. Further, it may be also possible to add other arbitrary components to the configuration of the present disclosure.

For example, the number and the kind of the components of the detection system 1 shown in FIG. 1 are merely provided for the illustration of the present disclosure, the present disclosure is not necessarily limited thereto. The scope of the present disclosure contains alternations and changes of the described configuration in which arbitrary components are added or combined or arbitrary components are omitted without meaningfully departing from the principle and the spirit of the present disclosure. Further, each component of the detection system 1 may be practiced in the manner of hardware, in the manner of software or in the manner of the combination of hardware and software.

Further, although the number of the detection processing devices 20 shown in each of the first embodiment to the third embodiment is one, the present disclosure is not limited thereto. The detection system 1 of the present disclosure may contain a plurality of detection processing devices 20. Each of the plurality of detection processing devices 20 may communicate with the same sensing device 10 to detect the state change of the inspection target 100 or respectively communicate the different sensing devices 10 to detect the state change of the inspection target 100.

Further, the number and the kind of the steps of the detection method S100 shown in FIG. 10 are merely provided for the illustration of the present disclosure, the present disclosure is not necessarily limited thereto. The scope of the present disclosure contains alternations and changes of the described configuration in which arbitrary steps are added or combined or arbitrary steps are omitted without meaningfully departing from the principle and the spirit of the present disclosure.

INDUSTRIAL APPLICABILITY

The detection system and the detection method of the present disclosure use the VCM (Voice Coil Motor) type vibration unit as an excitation unit for vibrating the inspection target, which includes the coil in which the electrical signal supplied from the driving circuit flows, the spring provided so as to be capable of vibrating and the magnet attached to the spring so as to be apart from the coil. Thus, it is unnecessary to constitute the vibration unit (the excitation unit) with an impulse-resistant material unlike the conventional art using the impulse hammer. Further, since the VCM type vibration unit can cause big vibration with a relatively low input voltage, it is unnecessary to apply a high input voltage to the vibration unit unlike the conventional art using the piezoelectric element. Thus, according to the present disclosure, it is possible to achieve simplification, downsizing and power saving of the detection system. For the reasons stated above, the present disclosure is industrially applicable.

The invention claimed is:

1. A detection system for detecting a state change of an inspection target, comprising:
a sensing device including:
a vibration unit for applying vibration to the inspection target, the vibration unit configured to be attached to the inspection target,
a driving circuit for supplying an electrical signal to the vibration unit for driving the vibration unit, and
a sensor for detecting vibration of the inspection target caused by the vibration applied from the vibration unit; and
a detection processing device for receiving vibration information related to the vibration of the inspection target detected by the sensor from the sensing device, calculating a coherence between vibration of the vibration unit and the vibration of the inspection target, and detecting the state change of the inspection target based on the vibration information when the coherence is equal to or more than 0.5,
wherein the vibration unit of the sensing device includes:
a case in form of a cylindrical member having a cover, a base which is configured to be attachable to the inspection target, and a cylindrical portion located between the cover and the base,
a coil fixedly attached on an upper surface of the base and in which the electrical signal supplied from the driving circuit flows,
a leaf spring provided so as to be capable of vibrating with respect to the case, and
a magnet assembly having a magnet holding portion having a cylindrical body portion and an upper plate provided on an upper end of the cylindrical body portion and a magnet fixed on a lower surface of the upper plate, and the magnet assembly attached to the leaf spring so as to be apart from the coil,
wherein the case contains the coil, the leaf spring, and the magnet assembly therein,
wherein the leaf spring has a ring shape with an outer peripheral portion held between the base and the cylindrical portion of the case, and a central portion containing a central opening portion,
wherein the magnet assembly is attached to the central portion,
wherein the central portion can vibrate with respect to the base so that the magnet assembly can vibrate with respect to the coil,
wherein the sensor is an acceleration sensor configured to be provided on the inspection target for detecting the vibration of the inspection target, and
wherein a lower end of the cylindrical body portion of the magnet holding portion is fixed on an upper surface of the central portion of the leaf spring.

2. The detection system as claimed in claim 1, wherein the detection processing device calculates a resonance frequency of the vibration of the inspection target from the vibration information and detects the state change of the inspection target based on a variation amount of the resonance frequency.

3. The detection system as claimed in claim 2, wherein the detection processing device includes a storage part for storing the resonance frequency of the vibration of the inspection target, and
wherein the detection processing device compares the calculated resonance frequency of the vibration of the inspection target with the resonance frequency of the vibration of the inspection target stored in the storage part in advance to calculate the variation amount of the resonance frequency and detects the state change of the inspection target when the variation amount of the resonance frequency is equal to or more than a predetermined threshold value.

4. The detection system as claimed in claim 1, wherein the driving circuit is configured to supply one of an impulse signal, a swept signal or a random signal to the vibration unit as the electrical signal.

5. The detection system as claimed in claim 1, wherein the detection system contains a plurality of sensing devices, and
wherein the detection processing device receives the vibration information related to the vibration of the inspection target from each of the plurality of sensing devices.

6. The detection system as claimed in claim 1, wherein the vibration unit and the sensor of the sensing device are contained in one case so that the sensing device is practiced as one device contained in the one case.

7. The detection system as claimed in claim 1, wherein the sensing device and the detection processing device are contained in one case so that the sensing device and the detection processing device are practiced as one device contained in the one case.

8. A detection method for detecting a state change of an inspection target, comprising:
applying vibration to the inspection target by supplying an electrical signal from a driving circuit to a vibration unit attached to the inspection target to drive the vibration unit;
detecting vibration of the inspection target caused by the vibration applied from the vibration unit by using a sensor;
calculating a coherence between vibration of the vibration unit and the vibration of the inspection target; and
detecting the state change of the inspection target based on the vibration of the inspection target detected by the sensor when the coherence is equal to or more than 0.5 by using a processor,
wherein the vibration unit includes:
a case in form of a cylindrical member having a cover, a base which is configured to be attachable to the inspection target, and a cylindrical portion located between the cover and the base,
a coil fixedly attached on an upper surface of the base and in which the electrical signal supplied from the driving circuit flows,
a leaf spring provided so as to be capable of vibrating with respect to the case, and
a magnet assembly having a magnet holding portion having a cylindrical body portion and an upper plate provided on an upper end of the cylindrical body portion and a magnet fixed on a lower surface of the upper plate, and attached to the leaf spring so as to be apart from the coil,
wherein the case contains the coil, the leaf spring, and the magnet assembly therein,
wherein the leaf spring has a ring shape with an outer peripheral portion held between the base and the cylindrical portion of the case, and a central portion containing a central opening portion,
wherein the magnet assembly is attached to the central portion,
wherein the central portion can vibrate with respect to the base so that the magnet assembly can vibrate with respect to the coil, wherein the sensor is an acceleration sensor configured to be provided on the inspection target for detecting the vibration of the inspection target, and wherein a lower end of the cylindrical body portion of the magnet holding portion is fixed on an upper surface of the central portion of the leaf spring.

9. The detection system as claimed in claim 1, wherein the case further has three extending portions formed on an outer peripheral surface of the base so as to extend in a radial direction of the base, and through-holes respectively formed in tip side portions of the three extending portions, and wherein the base can be fixed to the inspection target by means of screws passed through the through-holes of the base and respectively screwed with screw holes formed in the inspection target.

10. The detection system as claimed in claim 1, wherein the coil has a cylindrical shape and is located inside the central opening portion of the leaf spring.

11. The detection system as claimed in claim 1, wherein the magnet assembly has a yoke attached to a lower surface of the magnet, and wherein the magnet and the yoke are arranged in a central hollow portion of the coil so as to be apart from the coil.

12. The detection system as claimed in claim 1, wherein the coherence is expressed by the following equation:

$$\gamma^2 = \frac{|W_{xy}|^2}{W_{xx} \cdot W_{yy}}$$

wherein "$\gamma^2$" is the coherence, "$W_{xx}$" is a power spectrum of the vibration of the vibration unit, "$W_{yy}$" is a power spectrum of the vibration of the inspection target, and "$W_{xy}$" is a cross spectrum between the vibration of the vibration unit and the vibration of the inspection target.

13. The detection system as claimed in claim 1, wherein the upper plate of the magnet holding portion faces the cover of the case with a gap therebetween.

* * * * *